United States Patent [19]

Lindstrom

[11] Patent Number: 5,041,389
[45] Date of Patent: * Aug. 20, 1991

[54] ASSAYS FOR MYASTHENIA GRAVIS

[75] Inventor: Jon M. Lindstrom, Del Mar, Calif.

[73] Assignee: The Salk Institute for Biological Studies, San Diego, Calif.

[*] Notice: The portion of the term of this patent subsequent to Dec. 6, 2005 has been disclaimed.

[21] Appl. No.: 529,719

[22] Filed: May 29, 1990

Related U.S. Application Data

[63] Continuation of Ser. No. 185,496, Apr. 25, 1988, abandoned, which is a continuation of Ser. No. 816,383, Jan. 6, 1986, Pat. No. 4,789,640.

[51] Int. Cl.$^5$ ............................................ G01N 33/543
[52] U.S. Cl. ...................... 436/518; 424/1.1; 436/501; 436/504; 436/542; 436/804
[58] Field of Search ........................ 436/504, 501–503, 436/804, 536, 539, 540, 542, 518; 424/1.1

[56] References Cited

U.S. PATENT DOCUMENTS

Re. 30,059  7/1979  Lindstrom .......................... 23/230.3
4,202,875  5/1980  Lindstrom ............................... 424/1

OTHER PUBLICATIONS

McAllister et al., "Establishment of a Human Medullablastoma Cell Line," Int. J. Cancer 20, 206–212 (1977).
Syapin et al., "Neuronal Like Feature of TE671 Cells: Presence of a Functional Nicotinic Cholinergic Receptor," Brain Res. 231, 365–377 (1982).
Patrick and Stallcup, "Immunological Distinction between Acetylcholine Receptor and the Alpha-Bungaratoxin-binding Component on Sympathetic Neurons," Proc. Natl. Acad. Sci. (U.S.A.) 74, 4689–4692 (1977).
Tzartos et al., "Mapping of Surface Structures of Electrophorus Acetylcholine Receptor Using Monoclonal Antibodies," J. Biol. Chem. 256, 8435–8445 (1981).
Tzartos et al., "Specificities of Antibodies to Acetylcholine Receptors in Sera From Myasthenia Gravis Patients Measured by Monoclonal Antibodies," Proc. Natl. Acad. Sci. (U.S.A.) 79, 188–192 (1982).
Swanson et al., "Immunohistochemical Localization of Monoclonal Antibodies to the Nicotinic Acetylcholine Receptor in Chick Midbrain," Proc. Natl. Acad. Sci. (U.S.A.) 80, 4532–4536 (1983).
Smith et al., "Characterization of a Component in Chick Ciliary Ganglia that Cross-Reacts with Monoclonal antibodies to Muscle and Electric Organ Acetylcholine Receptor," J. Neuroscience 5, 2726–2731 (1985).
Lindstrom et al., "Production and Assay of Antibodies to Acetylcholine Receptors," Meth. Enzymol. 74, 432–460 (1981).
Tzartos et al., "Characteristics of Monoclonal Antibodies to Denatured Torpedo and to Native Calf Acetylcholine Receptors: Species, Subunit, and Region Specificity, "In The Press (1985).

*Primary Examiner*—Robert J. Hill, Jr.
*Attorney, Agent, or Firm*—Fitch, Even, Tabin & Flannery

[57] ABSTRACT

Improved asssays are provided for anti-acetylcholine receptor protein autoantibodies in the sera of patients with myasthenia gravis. The basis for the improved assays is the discovery that large quantities of acetylcholine receptor protein, that, for practical purposes in immunoassays, is immunologically indistinguishable from human muscle acetylcholine receptor protein, can be isolated from cells of the human medullablastoma-derived cell line TE671.

8 Claims, 2 Drawing Sheets

ASSAYS FOR MYASTHENIA GRAVIS

The United States Government has certain rights in the invention described and claimed herein as a result of support of work related to said invention under a grant from the United States National Institutes of Health.

This is a continuation of application Ser. No. 185,496, filed Apr. 25, 1988, abandoned, which is a continuation of application Ser. No. 816,383, filed Jan. 6, 1986, now U.S. Pat. No. 4,789,640.

TECHNICAL FIELD

The present invention relates to immunochemical assays for diagnosis of myasthenia gravis.

BACKGROUND OF THE INVENTION

Myasthenia gravis is an autoimmune disease. In a patient suffering from the disease, autoantibodies are generated against epitopes on acetylcholine receptors at neuromuscular junctions. This autoimmune response impairs neuromuscular transmission. This impairment causes the muscular weakness and fatigability which characterize the disease.

In my patents, U.S. Pat. Nos. 4,202,875 and RE 30,059, both of which are incorporated herein by reference, biochemical assays for the diagnosis of myasthenia gravis are described.

The assays in my above-cited patents involve immune precipitation, with anti-human immunoglobulin, of labeled acetylcholine receptor protein complexed with autoantibodies to the receptor protein from serum of a myasthenia gravis patient. The acetylcholine receptor protein (hereinafter "AChR") that is employed is part of a crude extract of mammalian muscle. The labeling of the AChR in these assays is accomplished by binding to the protein in the crude extract radioactively labeled, curaremimetic neurotoxins, such as Naja naja siamensis toxin and alpha-bungarotoxin. These toxins complex with the AChR by binding in the acetylcholine binding site on the protein.

While the assays described in my above-cited patents have found widespread commercial application and are at present the preferred assays for diagnosing myasthenia gravis, they involve a number of drawbacks. The preferred source for the AChR utilized in these assays is muscle from amputated human legs. This tissue is in short supply and, on account of a variety of legal complications, difficult to obtain for commercial applications even when available. Further, it is possible to obtain from the tissue only very small quantities of AChR suitable for the assays because the protein is present at only very low concentration in even healthy, unamputated tissue and because substantial proteolytic degradation of the protein occurs unavoidably before a crude extract of the muscle containing the protein can be isolated from the amputated tissue. Other, more plentiful, mammalian-muscle sources for the AChR are available; but these other sources are not entirely free of the drawbacks, of sparse amount and proteolytic degradation, of the human leg-muscle source and, more importantly, the AChR from non-human sources is less acceptable for the assays because human autoantibodies to human AChR cross react poorly with AChR's from other mammals (e.g., to the extent of only 2.1% in the case of AChR from denervated rat muscle, a typical alternative to AChR from human leg muscle).

The limited supply of human muscle AChR suitable for immunochemical assay has made it impracticable to assay for myasthenia gravis-related autoantibody in human serum other than by the immune precipitation assay using crude extracts of muscle described in my above-cited patents. The ready availability of a more plentiful source of AChR, that reacts with human autoantibodies to human muscle AChR to substantially the same extent as human muscle AChR itself, would make practical other, more sensitive immunoassay techniques, such as solid-phase and enzyme-linked immunosorbant assay (ELISA) techniques, for the diagnosis of myasthenia gravis.

The severity of muscle weakness in myasthenia gravis patients does not correlate closely with the concentration of anti-AChR antibodies in their sera. This is probably largely due to the multiple, complex mechanisms by which these antibodies impair transmission (reduction of number of receptors by antigenic modulation, complement-mediated focal lysis, direct impairment of AChR function by bound antibody) as well as the nature of neuromuscular transmission (occurring in an all or none fashion with a large safety factor to insure transmission) and the complex adaptive mechanisms which are available to the body to compensate for impaired neuromuscular transmission (increasing acetylcholine release, increasing the area of neuromuscular junctions).

In myasthenia gravis patents, autoantibodies bind to various epitopes on various regions of AChR. One of these regions is called the "main immunogenic region". This region is located on the extracellular surface of alpha-subunits of the AChR. Another of these regions is the acetylcholine (hereinafter "ACh") binding sites, which are also located on the alpha-subunits. In the average myasthenia gravis patient, about half of the anti-AChR-autoantibodies are directed at the main immunogenic region. Autoantibodies which bind to the main immunogenic region can cause antigenic modulation and fix complement in vivo and thereby reduce the number of ACh receptors. Antibodies which are directed at the ACh binding sites would, at very low concentrations, be very effective at directly impairing AChR function in neuromuscular transmission. It would be useful if one could measure not only total anti-AChR antibody concentration in sera of myasthenia gravis patients but also the fractions of these antibodies which are directed at the main immunogenic region and the ACh-binding sites of AChR.

The assay of my above-cited patents depends on the labeling to high specific activity of the muscle AChR by complexing with it radioactively labeled toxins which bind in the ACh-binding site of the protein. It has not been possible to assay specifically for autoantibodies directed against the ACh-binding site with the assay of my above-cited patents because, in such assays, the binding site and nearby areas are blocked by toxin and, thereby, the epitopes in the binding site, and other epitopes near it, are inaccessible to binding by autoantibody. The invention described herein, based on the discovery of a source for large quantities of easily isolated AChR which, for practical purposes, is immunologically indistinguishable from human muscle AChR, makes feasible immunoassay methods which do not require blocking of some epitopes on the AChR from binding by autoantibodies. Thus, with the present invention, measurement is possible of not only the total concentration of anti-AChR autoantibody in the sera of a patient, permitting diagnosis, but also the fractions of these antibodies directed at pathologically significant sites on the AChR, permitting better characterization of the patient's disease and improved basis for planning therapy to treat the disease.

McAllister et al., Int. J. Cancer 20, 206-212 (1977) reported the establishment of a cell line, designated TE671, Subline No. 2, from a human cerebellar medulloblastoma. This and equivalent AChR-producing cell lines are referred to in this specification as "the TE671 Line".

Syapin et al., Brain Research 231, 365-377 (1982) have characterized the cells of the TE671 Line as possessing mammalian neuronal nicotinic acetylcholine receptors. It is thought in the art that the proteins of such receptors are immunologically substantially different from (i.e., have low immunological cross-reactivity with) the AChR against which myasthenia gravis autoantibodies react (i.e., that antibodies against one of neuronal AChR and muscle AChR have little or no cross-reactivity with the other) (Patrick and Stallcup, Proc. Natl. Acad. Sci. (U.S.A.) 74, 4689 (1977); Swanson et al., Proc. Natl. Acad. Sci. (U.S.A.) 80, 4532 (1983); Smith et al., J. Neuroscience 5, 2726 (1985)).

Hybridomas which secrete rat monoclonal antibodies, including that designated mAb 35, to the main immunogenic region of muscle AChR have been described by Tzartos et al., J. Biol. Chem. 256, 8635-8645 (1981) and Proc. Natl. Acad. Sci. U.S.A. 79, 188 (1982). Other hybridomas, including that designated mAb 64, which secrete monoclonal antibodies against muscle AChR have also been developed (Tzartos et al., J. Neuroimmunology, 10, 235-253 (1986).

SUMMARY OF THE INVENTION

I have now found, unexpectedly, that the AChR on cells of the TE671 Line is, for practical purposes in immunoassays, immunologically indistinguishable from human muscle AChR and functions substantially the same as human muscle AChR derived from amputated human leg muscle in the immune precipitation assay, for diagnosing myasthenia gravis, that is described in my above-cited patents.

However, unlike the AChR derived from human leg muscle, the AChR from cells of the TE671 Line is readily available, in virtually unlimited amounts, at relatively high concentrations, and substantially free of heterogeneities and impurities due to proteolysis and other factors which lead to contamination of AChR from muscle sources.

This discovery makes practical substantially improved immunochemical assay systems for diagnosing myasthenia gravis.

DETAILED DESCRIPTION OF THE INVENTION

Figure 1:
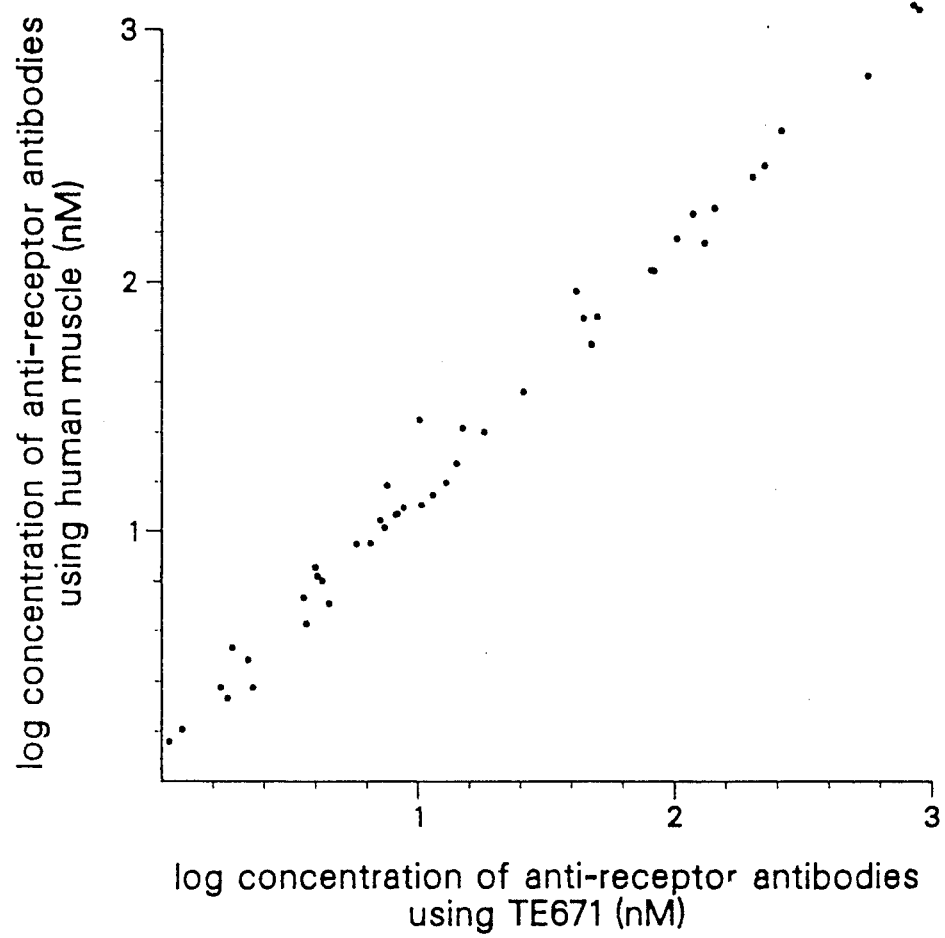
FIG. 1 illustrates the practical equivalence of AChR from human leg muscle and AChR from cells of the TE671 Line in the immune precipitation assay for serum anti-AChR autoantibodies described in my above-cited patents. The Figure is a graph of the logarithms (to base 10) of the anti-AChR autoantibody concentrations, in nM, in the sera of 45 myasthenia gravis patients, as determined in such an immune precipitation assay with human leg muscle AChR labeled with $^{125}$I-labeled alpha-bungarotoxin, as a function of the logarithms (to base 10) of the anti-AChR autoantibody concentrations, in nM, in the same sera as determined by an assay procedure that was the same but for replacement of human leg muscle AChR with AChR from cells of the TE671 Line.

In one aspect, the present invention entails improvements in the assays and processes disclosed in my above-cited patents for diagnosing myasthenia gravis. These improvements reside in the use of AChR derived from cells of the TE671 Line rather than AChR in crude muscle extracts.

As noted above, the assays and processes of my above-cited patents depend on immune precipitation of labeled AChR complexed with anti-AChR autoantibody in the serum of a person suffering from myasthenia gravis. The label on the AChR is a radioactively labeled, preferably an $^{125}$I-labeled, curaremimetic neurotoxin which binds with high affinity in the ACh binding site of the AChR. Curaremimetic toxins which can be employed to label AChR are naturally occurring proteins found in various poisonous reptiles, such as cobras and sea snakes. Many such toxins have been isolated and sequenced. See, e.g., Karlsson, Handbook of Experimental Pharmacology 52, 159-212 (1979). The preferred toxins for labeling are the so-called "long neurotoxins," as described by Karlsson, supra. Most preferred is alpha-bungarotoxin from Bungarus multicinctus.

In another aspect, the present invention involves processes for making an AChR, that is suitable for diagnosis of myasthenia gravis by immunoassays of anti-AChR autoantibodies in human serum, by culturing cells of the TE671 Line and for obtaining, from cells of the TE671 Line cultures, preparations of such AChR that are suitable for use in such immunoassays.

The culturing of cells of the TE671 Line, and obtaining preparations of AChR therefrom, are described in the Examples below.

By "cells of the TE671 Line" in the instant specification is meant (i) cells which are from a culture of any TE671 cell line, including a culture of subline no. 2 and including cultures of said subline that are on deposit at the ATCC under deposit no CRL 8805; or (ii) cells of a subculture of any culture specified in (i); or (iii) mutants of any of the cells specified in (i) or (ii); provided that said cells (under (i), (ii) and (iii)) produce AChR that, for practical purposes in immunoassays, is immunologically essentially the same as human muscle AChR. By "subculture" is meant a culture grown from cells of a culture (source culture) or any subculture of the source culture, regardless of the number of subculturings between the subculture of interest and the source culture. Mutants of cells specified in points (i) and (ii) of the definition of "cells of the TE671 Line " include mutants that arise spontaneously or from human intervention, as by repeated passaging, chemical treatment, irradiation, cell fusion, transformation, transfection, microinjection of nucleic acid into cell nucleii, and the like.

A method is illustrated in Example II for establishing that an AChR, for practical purposes in immunoassays, is immunologically essentially the same as human muscle AChR. Generally, this criterion is established if the anti-human muscle AChR antibodies in human sera are highly cross-reactive (to the extent of at least 50%) with the AChR of interest. Whether the criterion obtains can be ascertained by testing both human muscle AChR and the AChR of interest with a battery of monoclonal antibodies known to be reactive against antigenic determinants on one or the other of the AChR's; if all or nearly all (i.e., more than 9 of 10) of the antigenic determinants corresponding to the monoclonal antibodies are found in the testing to be on both of the AChR's, it can be concluded that, for practical purposes in immunoassays, the AChR's are immunologically indistinguishable (i.e., essentially the same). The high level of cross-reactivity with monoclonal antibodies which characterizes such immunologically indistinguishable AChR's also implies that, after correction for any known non-immunological factors, such as differences in affinity for labeled toxin in the immune precipitation assay described in my above-cited patents, the titer of anti-AChR antibody in a serum sample as determined in an immunoassay with human muscle AChR will be no more than 25% (plus or minus some due to inevitable experimental uncertainty) greater than the titer with AChR from cells of the TE671 Line. The relationship of anti-AChR antibody titers determined with two AChR's can be reliably ascertained by comparing the titers, determined in immune precipitation assays according to my above-cited patents and illustrated in Example II, with at least 10 sera which range over at least an order of magnitude in their anti-AChR antibody titers.

The AChR of cells of the cultures of the TE671 Line, subline 2, deposited at ATCC under deposit no. CRL 8805, is, for practical purposes in immunoassays, immunologically indistinguishable from human muscle AChR. Indeed, as illustrated by the data plotted in FIG. 1, after correction for differences in affinity for toxin (see Example II), the cross-reactivity of anti-AChR autoantibodies in human serum for AChR from cells of such cultures and AChR from human leg muscle is, within experimental error, nearly 100%; and the AChR's from these two sources are interchangeable in immunoassays of sera for diagnosing myasthenia gravis in persons suffering therefrom.

The invention further entails solid-phase immunoassays for autoantibodies against human muscle AChR, employing as antigen AChR derived from cells of the TE671 Line. Immunoassays for anti-AChR autoantibodies, which were not practicable heretofore because of the great difficulty and associated high cost of obtaining sufficient amounts of human muscle AChR, are made readily available by the availability of AChR from TE671 cells. The solid-phase immunoassays are carried out with AChR from cells of the TE671 Line following methods known in the solid-phase immunoassay art.

A "substrate" for the solid-phase immunoassay is made by affixing the AChR covalently or non-covalently to a solid support by any of numerous methods known in the immunoassay art. Among the solid supports known in the art that can be employed are those made of polyethylene, polypropylene, polybutylene, polystyrene, polymethacrylate, polyacrylamide, other synthetic polymeric materials to which the AChR can be affixed, glass, nitrocellulose, cellulose, and agarose. The solid support can be a "macroporous" gel-type support such as formed by, for example, certain agarose materials (e.g., Sephacryl S-500 from Pharmacia, Inc., Piscataway, N.J., U. S. A.). The solid support can be in the form of microparticles such as microspheres or beads (e.g., "latex" beads) or can be the inside wall of a tube, such as a microfuge tube or a well of a microtiter or Millititer plate. The solid support with AChR bound, after appropriate washings and incubation with materials to reduce background by blocking sites on the support not occupied by AChR, as understood in the art, and after optional preincubation with a substance (such as a curaremimetic neurotoxin, a small cholinergic ligand or an antibody) which blocks certain epitopes on the AChR, is incubated with serum or, more commonly, a dilution thereof in a suitable buffer, as illustrated in Example III and otherwise understood in the art. Optionally, prior to being incubated with the solid-phase-bound AChR, the serum (or dilution) can be mixed with a substance (such as a curaremimetic neurotoxin, a low molecular weight cholinergic compound, or an antibody) at concentrations sufficient to out-compete any autoantibody in the serum from binding to certain epitopes on the AChR. Autoantibody in the serum against epitopes on the AChR that are not blocked by such epitope-blocking substances that might be employed will bind to the AChR. After appropriate washing as understood in the art, the autoantibody bound to the AChR is then detected by incubation with a labeled anti-autoantibody or labeled Protein A from Staphyloccocus aureus, or any protein or other substance which is labeled for detection and will bind to autoantibody but not significantly to other substances in the system.

Preferably, labeled anti-autoantibody is employed for detection. Typically the labeled anti-autoantibody will be provided as labeled, polyclonal anti-human IgG. However, polyclonal subclass specific anti-immunoglobulins, such as anti-human IgG1 or anti-human IgM, or anti-human immunoglobulin that is not specific for a particular class or subclass, can also be used. The antisera employed for detection will typically be from goat, rabbit, rat or mouse, although other, non-human mammalian species may also be used as the source.

If the solid-phase immunoassay is an ELISA, the label on the anti-human immunoglobulin, S. aureus Protein A or other substance bound to anti-AChR autoantibody will be an enzyme, such as an acid or alkaline phosphatase, a peroxidase, or a beta-galactosidase, and detection will be by means of a product produced in a reaction catalyzed by the enzyme label, as known in the art.

If the solid-phase immunoassay is not an ELISA and there is a label on the anti-immunoglobulin, S. aureus Protein A or other substance, the label will usually be different from an enzyme. Such non-enzyme labels include radioactive atoms, chromophores or fluorophores, and biotin; detection methods for each of these labels, as well as other labels known in the art that may also be employed, are known in the art. Preferred is $^{125}$I-labeling.

In another alternative, the AChR with anti-AChR autoantibody bound and with unlabeled anti-autoantibody also bound, is detected by incubation with labeled S. aureus Protein A followed by detection of the label on the Protein A. The label on the Protein A can be an enzyme or any of the other labels described above or otherwise known in the art.

Another aspect of the invention is a method to characterize the anti-AChR autoantibodies of a patient suffering from myasthenia gravis according to the titers of fractions of such autoantibodies that bind to various subsets of epitopes on the AChR. This method comprises carrying out at least two of four solid-phase immunoassays on the serum of a patient, which immunoassays are substantially the same except that: one is with solid-phase bound AChR alone; one with solid-phase bound AChR incubated with a monoclonal antibody (e.g. mAb 35) to the main immunogenic region, either prior to or simultaneously with incubation with a serum sample; one with solid-phase bound AChR incubated, prior to or simultaneously with incubation with a serum sample, with a curaremimetic neurotoxin; and one with solid-phase bound AChR incubated, prior to or simultaneously with incubation with a serum sample, with a low molecular weight compound (e.g., nicotinic cholinergic ligand such as carbamylcholine) that binds tightly in the ACh binding site but does not, like the neurotoxins, block nearby sites. The assay with AChR alone will yield information on the titer of all autoantibodies to epitopes on the AChR. The assay together with the monoclonal antibody to the main immunogenic region will yield information on titer of autoantibodies to epitopes outside the main immunogenic region of the AChR. The assay together with the curaremimetic neurotoxin will yield information on the titer of autoantibodies to epitopes outside the ACh binding site and nearby sites blocked by the toxin. Finally, the assay together with the low molecular weight compound which binds in the ACh binding site will yield information on titer of autoantibodies to the ACh binding site itself. Usually in these assays, the incubation of the epitope-blocking substance with AChR is accomplished by combining the blocking substance with the serum sample, which is incubated with the immunoassay substrate (i.e., solid support with AChR bound), at a high enough concentration in the sample to out-compete in binding nearly all autoantibody in the sample that might bind to the same epitope or epitopes as the blocking substance.

As indicated above, the basis for the solid-phase immunoassays is a substrate material to which AChR derived from cells of the TE671 Line is complexed by covalent or non-covalent binding. These solid-phase substrates with AChR complexed are also part of the instant invention. These substrates are prepared by any means known in the art for affixing an antigen to a solid support in a manner suitable for solid-phase immunoassay for antibody against the antigen.

The substrates of the invention, with AChR from cells of the TE671 Line complexed, facilitate the preparation of kits for the diagnosis of myasthenia gravis. Said kits preferably comprise a substrate of the invention and other components necessary for a solid-phase immunoassay of a patient's serum for anti-AChR autoantibodies. Such kits are also encompassed by the present invention.

The invention is described in greater detail in the following examples.

EXAMPLE I

Culturing Cells of the TE671 Line

Any techniques in the art for culturing mammalian cells can be employed to culture cells of the TE671 Line.

A preferred technique for growing TE671 cells is to use Iscove's modified Dulbecco's minimal essential medium (Irvine Scientific, Santa Ana, California) containing 10% fetal bovine serum in an atmosphere of 90% air and 10% $CO_2$ at 37° C.

Small volumes are grown in 35 mm dishes using an innoculum of $3 \times 10^5$ cells in 1.5 ml of medium. After three days the medium is changed, and optimal AChR yield is obtained on day six or seven.

For large volumes, plastic roller bottles (Falcon Labware, Becton-Dickinson, Inc., Oxnard, Calif. U.S.A.) are used. In the case of 850 cm$^2$ bottles, $3 \times 10^7$ cells are inoculated in 150 ml of medium; whereas, for 1750 cm$^2$ bottles, $6 \times 10^7$ cells are inoculated in 300 ml of medium. The medium is changed on day five, and AChR yield is optimal on days nine to ten.

EXAMPLE II

Isolation and Characterization of Acetylcholine Receptor From Cells of the TE671 Line and Use of Said Receptor in Immune Precipitation Assays AChR has typically been isolated from the cultures from six or seven 850 cm$^2$ roller bottles at a time, although much larger volumes of culture can easily be processed simultaneously. The following procedure has been used routinely for the isolation of AChR from cultures of cells of the TE671 Line, subline No. 2, samples of which are on deposit at the ATCC under deposit No. CRL 8805:

To each 850 cm$^2$ bottle of culture on day nine or ten, after growth as described in Example I, is added 25 ml of harvest buffer (100 mM NaCl, 10 mM Na phosphate buffer, 10 mM NaN$_3$, 15 mM EDTA (ethylenediaminetetraacetic acid), 2 mM PMSF (phenylmethanesulfonylfluoride), 15 mM IAA (iodoacetic acid), and 5 mM benzamidine, pH 7.5). The bottles are then vigorously shaken until the cells come off of the plastic. The buffer and cells are collected in a bottle on ice, and the roller bottles are rinsed from bottle to bottle with an additional 100 ml of harvest buffer, which is then pooled with the rest. A Polytron homogenizer is then used to disrupt the cells for 15 seconds at a speed just below that at which foaming occurs. Membranes and other particulates are collected by centrifuging the homogenate for 30 minutes at 45,000 rpm in a Beckman Ti50.2 rotor (Beckman Instruments, Inc., Spinco Division, Palo Alto, Calif., U.S.A.) (302,000 X g) at 4° C. Typically, about 1.5 gm of pellet is recovered per 850 cm$^2$ bottle. The pellets are placed in four volumes of extraction buffer (10 mM Na phosphate, 5 mM EDTA, 5 mM EGTA (ethylene glycol, bis-(2-aminoethylether)-N,N,N',N'-tetraacetic acid), 5 mM IAA, 5 mM benzamidine, 2 mM PMSF, 2% Triton X-100, pH 7.5) and gently suspended with the Polytron for 15 seconds. After extraction for 30 minutes with gentle shaking at 4° C., the preparation is centrifuged as before. The supernate typically contains AChR at about $1.1 \times 10^{-8}$ M in a yield of about $6.6 \times 10^{-11}$ moles per 850 cm$^2$ bottle. A comparable crude extract of minced muscle tissue contains AChR at only about $2 \times 10^{-10}$ M to about $2 \times 10^{-9}$ M and generally less than $1 \times 10^{-9}$ M.

Immune precipitation experiments were carried out on sera from 45 patients essentially as described in my above-cited patents using AChR at 2 nM from the 2% Triton X-100 extracts (as described above in this Example) of either TE671 cells or muscle from amputated human leg. The concentration of AChR in the TE671 cell extract was reduced to 2 nM by dilution with assay buffer (100 mM NaCl, 10 mM Na phosphate buffer, 10 mM NaN$_3$, 0.5% Triton X-100, pH 7.5). The muscle extract employed was a rare one, in which the concentration of AChR reached about 2 nM, and was used without dilution. More typically, the concentration of AChR in the muscle extracts would have been significantly lower and would have been increased by a standard technique (e.g., employing an Amicon concentrator) (Amicon, Danvers, Mass., U.S.A.) until the AChR concentration reached 2 nM.

The AChR's were labeled by combining the AChR solutions with an amount of a 2 micromolar solution of $^{125}$I-labeled alpha-bungarotoxin, in Na phosphate buffer, pH 7-7.5, to bring the $^{125}$I-labeled alpha-bungarotoxin concentration to 4 nM, and then incubating the resulting solutions for 4 hours at 4° C.

Analyses were carried out in triplicate on various dilutions with assay buffer of each serum being tested. Supplementary normal human serum was added to each sample so that there was a total of 5 microliters of serum in the final reaction mix. The purpose of the dilutions is to bring the concentration of anti-AChR autoantibody from a serum being tested within the measurable range of the assay and preferably within a range such that 10-20% of the labeled AChR in an assay solution is complexed by anti-AChR autoantibody. The dilutions employed may vary widely, but will be determined by taking into account the concentration of labeled AChR in the assay solution with which serum samples are combined and the fact that anti-AChR autoantibodies in sera of persons suffering from myasthenia gravis can be as high as about 1,500 nM. The supplementary normal serum is added so that the total amount of immunoglobulin in each sample is approximately the same.

Each of the three samples of each dilution of each test serum was combined with 100 microliters of the labeled AChR solution (2 nM) and the combination was incubated overnight at 4° C. Then 100 microliters of goat anti-human IgG (at a concentration sufficient to precipitate all IgG in 5 microliters of serum) was added and the resulting solution incubated for 30 minutes at 4° C. to precipitate all of the human serum IgG. After addition of 1 ml of assay buffer, the solution was centrifuged for two minutes at 10,000×g at 20° C. The supernatant was aspirated and the pellet washed twice, each time with 1 ml of assay buffer, by vortexing followed by 2 minute centrifugation at 10,000×g and 20° C. and aspiration of supernatant. Finally, the $^{125}$I in the pellet was determined by gamma-counting by a standard technique.

A blank amount, obtained using 5 microliters of normal serum, was subtracted from the amount determined for each sample.

The results of this experiment are illustrated in FIG. 1. In the Figure, the logarithm of the serum concentration of anti-AChR antibody precipitable by the anti-IgG, determined with human leg muscle AChR, is plotted as a function of the logarithm of the same concentration determined with the TE671 cell-derived AChR. The difference from equality of these two concentrations for each sample is accounted for by experimental error in the assay procedures and the reported difference between the dissociation constant of alpha-bungarotoxin complexed with AChR from human muscle ($1.8 \times 10^{-10}$ M, Luky and Morgan-Hughes, Ann. N.Y., Acad. Sci. 377, 61 (1981)) and that of alpha-bungarotoxin complexed with AChR from cells of the TE671 Line, subline no. 2 ($1.4 \times 10^{-9}$ M, Syapin et al., supra). The results of the experiment establish that serum autoantibodies against AChR from human muscle are greater than 70% cross-reactive with the AChR that was derived from TE671 cells and that, for practical purposes in immunoassays, the AChR's from the two sources can be used interchangeably.

As further support for the conclusion that the AChR's from the two sources are immunologically the same, at least for purposes of immunoassays, comparisons of AChR from human leg muscle with AChR from cells of the TE671 Line using monoclonal antibodies have not identified any antigenic determinant on the leg muscle-derived AChR that is not also on the TE671 cell-derived AChR.

EXAMPLE III

Use of Acetylcholine Receptor From Cells of the TE671 Line in Solid-Phase Immunoassays for Serum Autoantibodies Against Human Muscle Acetylcholine Receptor (A) Preparation of Solid-Phase with AChR Affixed Thereto.

Following the procedure described in Example II, but employing eight volumes rather than four volumes of extraction buffer, relative to the volume of pellets, 75 ml of Triton X-100 extract of AChR was obtained from cultures of cells of the TE671 Line, subline No. 2, of which samples are deposited at the ATCC under deposit No. CRL 8805. The AChR of the extract was then affinity-purified on toxin-agarose following the procedure of Lindstrom et al, Methods in Enzymology 74C, 432-459 (1981) as follows:

The Triton X-100 extract, containing about 5.9 X 10 M AChR, was recirculated overnight at 4° C. through a 3 ml column of toxin-agarose (0.5 mg Naja naja siamensis toxin III per ml of Sepharose C14B (Pharmacia, Inc., Piscataway, N.J., U.S.A.)) at a rate of 42 ml/hr. (Improved binding of TE671 AChR, with its apparently low affinity for the toxin, could probably have been obtained by using an affinity column containing 5-10 mg/ml of toxin.) The column was then washed with 10 ml of 0.1% Triton X-100 in 10 nM Na phosphate buffer, pH 7.5. Elution of AChR was achieved using 1 M carbamylcholine in elution buffer (0.1% Triton X-100, 100 mM NaCl, 10 mM NaN3, 10 mM Na phosphate, pH 7.5) recirculated in separate 3 ml aliquots at 4° C. for 8 hrs, then 18 hrs, and finally 36 hrs. The three eluates were then combined and dialyzed at 4° C. against elution buffer to remove carbamylcholine. Under these conditions, 0.226 nmoles of AChR, of the 0.44 nmoles applied, were bound, and a total of 0.101 nmoles were eluted in 8.1 ml of a 13.8 nM solution.

AChR concentration is assayed by immune precipitation of the AChR labeled with $^{125}$I-labeled-alpha-bungarotoxin (Lindstrom et al., supra). The assay can be carried out with a polyclonal anti-AChR antiserum, as from a rabbit, mouse or rat, with serum from a myasthenia gravis patient with a high serum titer of anti-AChR autoantibody, or with an anti-AChR monoclonal antibody, such as mAb 35 or mAb 64.

Figure 2:
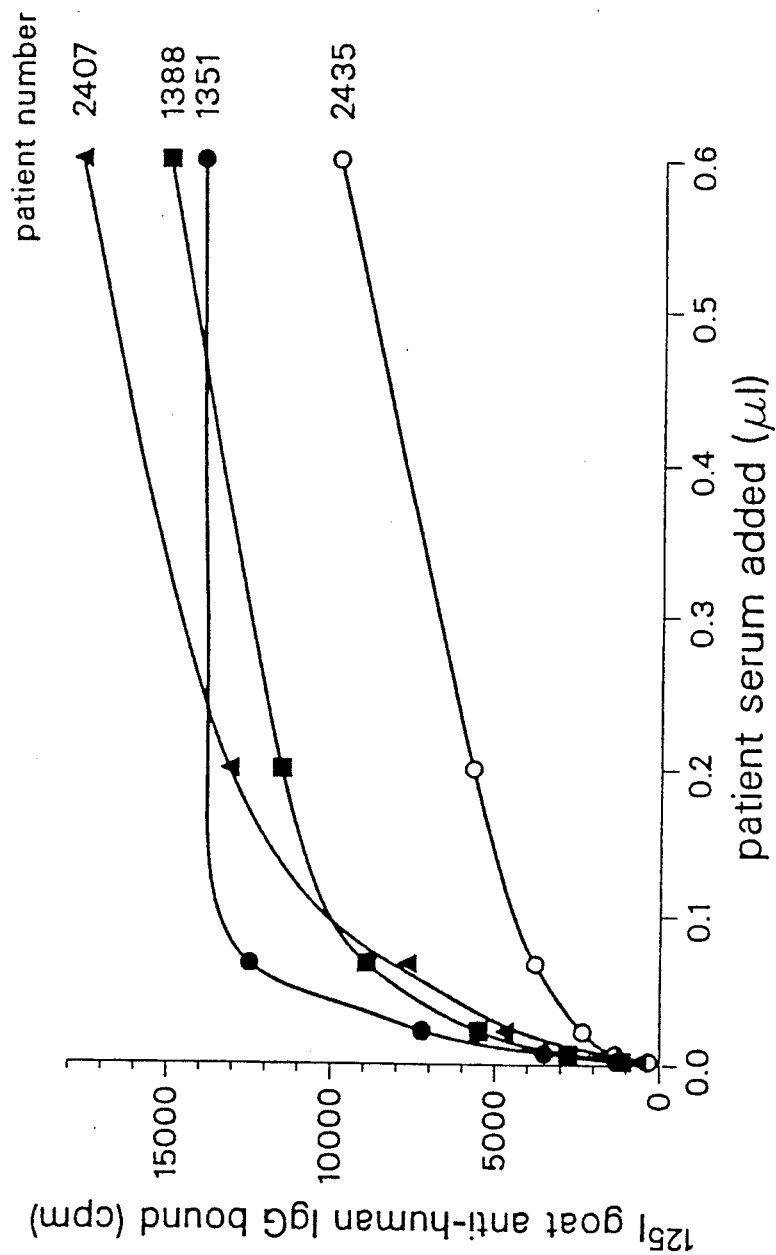
FIG. 2 illustrates the data from immunoassays, for serum anti-AChR autoantibody in various myasthenia gravis patients, employing AChR from cells of the TE671 Line as the solid-phase bound antigen and $^{125}$I-labeled goat anti-human IgG for detection of antigen-bound autoantibody.

The purified AChR was bound to wells of a Millipore Millititer-HA 96 well filtration plate (Millipore, Bedford, Mass. U.S.A., Cat. No. STHA096NS) by applying 30 microliter aliquots overnight at 4° C (more than 400 fmoles AChR can be bound per well). Further binding was then quenched by adding 50 microliters of quench buffer (3% bovine serum albumin (BSA), 0.2% Tween-20, 100 mM NaCl, 10 mM NaN3, 10 mM Na phosphate pH 7.5) and letting stand for 2 hrs at 4° C. All of the liquid was then removed using a Millipore Millititer Vacuum Holder (Millipore Cat. No. XX 28096 00). Then a sample of a test serum (diluted appropriately to 30 microliters with quench buffer) was added to each well and let stand for 4 hours at 4° C. After removing the liquid as before, the wells were washed twice with 300 microliters of the quench buffer. Then $^{125}$I-labeled, affinity-purified goat anti-human IgG (30 microliters of a $1 \times 10^{-8}$ M solution in quench buffer) was added to the wells and let stand for 2 hours at 4° C. After removing this liquid and washing twice with 300 microliters of quench buffer, the filters were punched out of the wells (using a Millipore filter punch, Millipore Cat. No. XX 28096 20) and placed in a gamma-counter for gamma-counting by a standard technique. Normal human serum diluted in quench buffer was employed as control, and values for gamma emission reflecting binding of anti-ACHR autoantibody to AChR in test samples were obtained by subtracting the appropriate normal serum values from the values obtained for the test samples. Data obtained using this assay are shown in FIG. 2, wherein the ordinate is in units of counts per minute (cpm) from gamma emission and the abscissa is in units of microliters of test serum assayed.

On the basis of standards, in which normal human IgG is applied to the wells instead of AChR and the gamma emission from $^{125}$I-labeled anti-human IgG bound to the normal human IgG is measured, the concentration of myasthenia gravis patient serum autoantibodies against AChR can be calculated, in terms of grams or moles of autoimmune IgG/liter of patient serum, from the gamma emission data obtained as described above. The results can also be normalized to values obtained using the immune precipitation assay illustrated in Example II. Rather than using only anti-IgG to detect autoantibody bound to AChR, labeled subclass-specific antisera could be used and, thereby, the subclass distribution of the autoantibodies determined.

Apparently, about half of the AChRs which bind to the millititer plate wells retain their ability to bind $^{125}$I-labeled alpha-bungarotoxin. Thus, the fraction of autoantibodies in a patient's serum which are directed at or near the ACh binding site can be determined by carrying out two immunoassays on the serum: one as described above and one wherein the AChR bound to wells is incubated with serum samples which include an excess of alpha-bungarotoxin (or similar toxin), or a small cholinergic ligand such as carbamylcholine, to out-compete from binding, at the toxin or cholinergic ligand binding sites, substantially all of any autoantibody in the serum that binds to such sites. From the results of the two assays, the fraction of autoantibodies which are inhibited from binding to the AChR by the toxin or cholinergic ligand can be determined; this fraction is, or is a close approximation to, the fraction of autoantibodies directed at and near the ACh binding site. Similarly, the fraction of the autoantibodies directed to the main immunogenic region of the AChR can be determined by determining the fraction which are inhibited from binding to AChR upon incubating the AChR bound to the wells with serum combined with an excess of a monoclonal antibody to the main immunogenic region of the AChR, such as the rat monoclonal antibody mAb 35.

Deposit of Cell Lines

Cultures of the TE671 Cell Line (Subline No. 2) and of the hybridoma lines mAb 35 (which produces monoclonal antibody mAb 35) and mAb 64 (which produces monoclonal antibody mAb 64) have been deposited at the American Type Culture Collection, Rockville, Md., U.S.A. (ATCC) under the terms of the Budapest Treaty on the Deposit of Microorganisms for the Purposes of Patent Procedure and the Regulations promulgated thereunder. The cultures of TE671 cells have been assigned ATCC deposit no. CRL 8805. The cultures of hybridoma mAb 35 have been assigned ATCC deposit no. HB 8857. The cultures of hybridoma mAb 64 have been assigned ATCC deposit no. HB8987. Samples of all three of the cultures are and will be available to industrial property offices and other parties legally entitled to receive them in accordance with said Treaty and Regulations and otherwise in accordance with the patent law of the United States.

While the present invention has been described herein with some particularity, those of skill will recognize numerous modifications and variations that remain within the spirit of the invention. These modifications and variations are within the scope of the invention as described and claimed herein.

what is claimed is:

1. In an immunoassay for myasthenia gravis comprising contacting serum of a person suspected of having myasthenia gravis with a complex of AChR and toxin labeled with a radioactive isotope and measuring the amount of anit-AChR autoantibodies bound to the radioactive complex resulting from said contacting, the improvement wherein the AChR is derived from cells of the TE671 Line.

2. The immunoassay according to claim 1 wherein the radioactivity labeled toxin is a curaremimetic neurotoxin labeled with $^{125}$I.

3. The immunoassay according to claim 2 wherein the toxin is alpha-bungarotoxin.

4. The immunoassay according to claim 3 wherein the AChR is derived from a culture of cells of the TE671 Line, subline No. 2, or a subculture thereof.

5. The immunoassay according to cliam 4 wherein the AChR is derived from a culture deposited at the ATCC under deposit no. CRL 8805 or a subculture thereof.

6. In a process for diagnosing myasthenia gravis, which comprises contacting serum of a person suspected of having myasthenia gravis with a solid-phase form of AChR, and measuring the amount of anti-AChR autoantibodies bound to the AChR resulting from said contacting, the improvement wherein the AChR employed in the process is derived from cells of the TE671 Line.

7. The process according to claim 6 wherein the AChR employed in the immunoassay is derived from cells of the TE671 Line, subline No. 2, or a subculture thereof.

8. The process according to claim 7 wherein the AChR employed in the immunoassay is derived from cells of a culture on deposit at the ATCC under deposit no. CRL 8805 or a subculture thereof.

* * * * *

UNITED STATES PATENT AND TRADEMARK OFFICE
CERTIFICATE OF CORRECTION

PATENT NO. : 5,041,389

DATED : August 20, 1991

INVENTOR(S) : Jon M. Lindstrom

It is certified that error appears in the above-identified patent and that said Letters Patent is hereby corrected as shown below:

Title Page:
Under Other Publ., under "Smith et al." change "antibodies" to --Antibodies--.

Column 2, line 29, change "patents" to --patients--.

Column 3, line 8-9, change "medulloblastoma" to --medullablastoma--.

Column 3, line 33, after "1986)" insert --)--.

Column 4, line 48, change "no" to --no.--.

Column 4, line 51, change "(')" to --(i)--.

Column 7, line 63, change "techniques" to --technique--.

Column 9, line 11, change "$^{125}$-labeled" to --$^{125}$I-labeled--.

Column 10, line 32, change "5.9 x 10 M" to --5.9 x $10^{-9}$M--.

Column 11, line 17, change "ACHR" to --AChR--.

Column 12, line 1, change "Deposit" to --Deposits--.

Column 12, line 27, change "what" to --What--.

Claim 1, Column 12, line 32, change "anit" to --anti--.

Claim 5, line 44, change "Cliam" to --Claim--.

UNITED STATES PATENT AND TRADEMARK OFFICE
CERTIFICATE OF CORRECTION

PATENT NO. : 5,041,389

DATED : August 20, 1991

INVENTOR(S) : Jon M. Lindstrom

It is certified that error appears in the above-identified patent and that said Letters Patent is hereby corrected as shown below:

Column 7, line 63, after "technique" insert --known--.

Signed and Sealed this

Second Day of March, 1993

*Attest:*

STEPHEN G. KUNIN

*Attesting Officer*    *Acting Commissioner of Patents and Trademarks*